(12) United States Patent
Alpenfels

(10) Patent No.: US 7,731,829 B2
(45) Date of Patent: Jun. 8, 2010

(54) ELECTROPHORESIS GEL AND METHOD OF MAKING SAME

(75) Inventor: William F. Alpenfels, Del Mar, CA (US)

(73) Assignee: Expedion, Inc., San Diego, CA (US)

(*) Notice: Subject to any disclaimer, the term of this patent is extended or adjusted under 35 U.S.C. 154(b) by 652 days.

(21) Appl. No.: 11/612,073

(22) Filed: Dec. 18, 2006

(65) Prior Publication Data
US 2007/0187252 A1 Aug. 16, 2007

Related U.S. Application Data

(60) Provisional application No. 60/772,664, filed on Feb. 13, 2006.

(51) Int. Cl.
*G01N 27/453* (2006.01)

(52) U.S. Cl. .................................. 204/469; 204/616

(58) Field of Classification Search .............. 204/450, 204/456, 465, 469, 600, 606, 615, 616; 435/288.4
See application file for complete search history.

(56) References Cited

U.S. PATENT DOCUMENTS

| | | | |
|---|---|---|---|
| 4,654,132 A | 3/1987 | Takagi et al. | |
| 4,693,804 A * | 9/1987 | Serwer | 204/466 |
| 5,074,980 A * | 12/1991 | Vasta-Russell et al. | 204/461 |
| 5,656,145 A | 8/1997 | Nguyen et al. | |
| 5,753,095 A | 5/1998 | Alpenfels et al. | |
| 6,140,326 A | 10/2000 | Lazzari et al. | |
| 6,406,602 B1 | 6/2002 | Cahill et al. | |
| 6,533,967 B1 * | 3/2003 | Ritchie et al. | 252/604 |
| 6,621,086 B1 * | 9/2003 | Appleby | 250/492.1 |
| 6,878,257 B2 | 4/2005 | Manusu et al. | |
| 7,033,477 B2 | 4/2006 | Alpenfels et al. | |
| 2003/0000839 A1 * | 1/2003 | Manusu et al. | 204/618 |
| 2003/0141190 A1 | 7/2003 | Alpenfels et al. | |
| 2003/0232341 A1 | 12/2003 | Casey et al. | |
| 2004/0178072 A1 * | 9/2004 | Goodall et al. | 204/459 |

OTHER PUBLICATIONS

Institute of Medicine (U.S.). Committee on Food Chemicals Codex, Edition: 5, illustrated. Published by National Academies Press, 2003. ISBN 0309088666, 9780309088664. p. 975.*

* cited by examiner

*Primary Examiner*—Alex Noguerola
(74) *Attorney, Agent, or Firm*—Stephen C. Beuerle; Procopio, Cory, Hargreaves & Savitch LLP

(57) ABSTRACT

An electrophoresis gel has a colored or pigmented loading area at one edge having a plurality of sample wells for receiving samples, the loading area extending beyond the ends of the wells so that the wells can be visually differentiated from the surrounding colored material in the loading area. The remainder of the gel is transparent or substantially transparent.

12 Claims, 1 Drawing Sheet

US 7,731,829 B2

ELECTROPHORESIS GEL AND METHOD OF MAKING SAME

RELATED APPLICATION

The present application claims the benefit of U.S. provisional patent application Ser. No. 60/772,664 entitled IMPROVED ELECTROPHORESIS GEL CONTAINING INSOLUBLE PIGMENT, filed on Feb. 13, 2006, which is incorporated herein by reference in its entirety.

BACKGROUND

1. Field of the Invention

The present invention relates generally to electrophoresis gel assemblies and to methods of making an electrophoresis gel.

2. Related Art

Electrophoresis gels are use routinely in laboratories for the separation and analysis of proteins, poly-nucleic acids (such as DNA and RNA) and carbohydrates. The gels are typically uniformly transparent. They contain a sample loading area, such as holes in gels run horizontally or sample pockets in gels run vertically. These sample pockets are typically formed using a comb-shaped device inserted into the top of the mold when forming the gel. Because the gel is transparent and has about the same refractive index as the solutions used to fill the wells before loading samples onto them, it is difficult to see where the wells actually are. The smaller the sample wells, the more challenging it is to actually load samples in the correct place. Further, since samples are usually loaded near the bottom of the sample well using pipettes, knowing where the bottom of the well is would be useful.

Some improvements to gels have been made to improve loading. For example, U.S. Pat. No. 5,656,145 issued to Nguyen uses a loading guide so one can direct the samples into the wells without seeing them. Pre-cast gel products are also made with an outline printed on the outside of the mold in which the gel is contained, showing where the wells are supposed to be. These methods are cumbersome or imprecise, and complicated by the fact that the gel fingers dividing the wells may move. Other efforts have been made using visible or fluorescent soluble dyes in the loading area. These dyes tend to diffuse out of the loading area, may migrate down the gels during electrophoresis, or bleach out of the gel during polymerization (especially photo-polymerization). Finally, alternate structures, such as plastic ribs or walls have been used to divide sample-loading wells, making them easier to see. Examples of these can be found in U.S. Pat. No. 6,878,257 to Manusu and U.S. Patent application 20030141190 by Alpenfels. While useful, these structures are more expensive to make, can inhibit polymerization of the gel fingers, and can block the current flow, which in turn causes samples separated in adjacent lanes to merge together. Further, since samples are usually loaded near the bottom of the sample well using pipettes, knowing where the bottom of the well is would be useful. If one tries to expel sample from the pipette into the well while it is touching the top of the gel surface, the sample expels with too much force when the pipette is raised, often ruining the quality of the resulting separation. None of the prior art helps to know such information with certainty.

SUMMARY

The present invention solves these problems and others by differentiating the loading area of the electrophoresis gel to make the sample wells easier to be seen. Insoluble pigmented materials are added to the gel in the loading area to visually differentiate the loading area and sample wells. In one embodiment, a gel is generally rectangular and has a plurality of sample wells in a loading area at first edge of the gel, and insoluble pigmented material is added to the gel in the loading area extending from the first edge of the gel beyond the lower ends of the wells. In one embodiment, the remainder of the gel area extending from the loading area to the opposite edge of the gel is transparent or substantially transparent.

A method of making an electrophoresis gel is provided in one embodiment, which comprises filling a first portion of a mold with a gel-forming solution to a level corresponding to a desired lower edge of a loading area, allowing the gel-forming solution to set, filling a second, loading area portion of a mold extending from the lower edge of the loading area with a pigmented gel-forming solution containing insoluble pigmented material, inserting a comb for forming sample wells into the pigmented solution, allowing the pigmented gel-forming solution to set, and removing the comb.

In one embodiment, the insoluble pigmented material is a dry, powder-coat paint of any desired color, such as red, blue or the like, and may comprise colored plastic beads such as polyester dry powder-coat paints. The concentration of the insoluble pigmented material in the gel-forming material may be of the order of 0.1% to 1%, with the lower end of the range used for intense colors such as bright red and the upper end of the range used for soft colors such as white. The insoluble pigmented material does not interfere with the electrophoretic separation.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Figure 1:
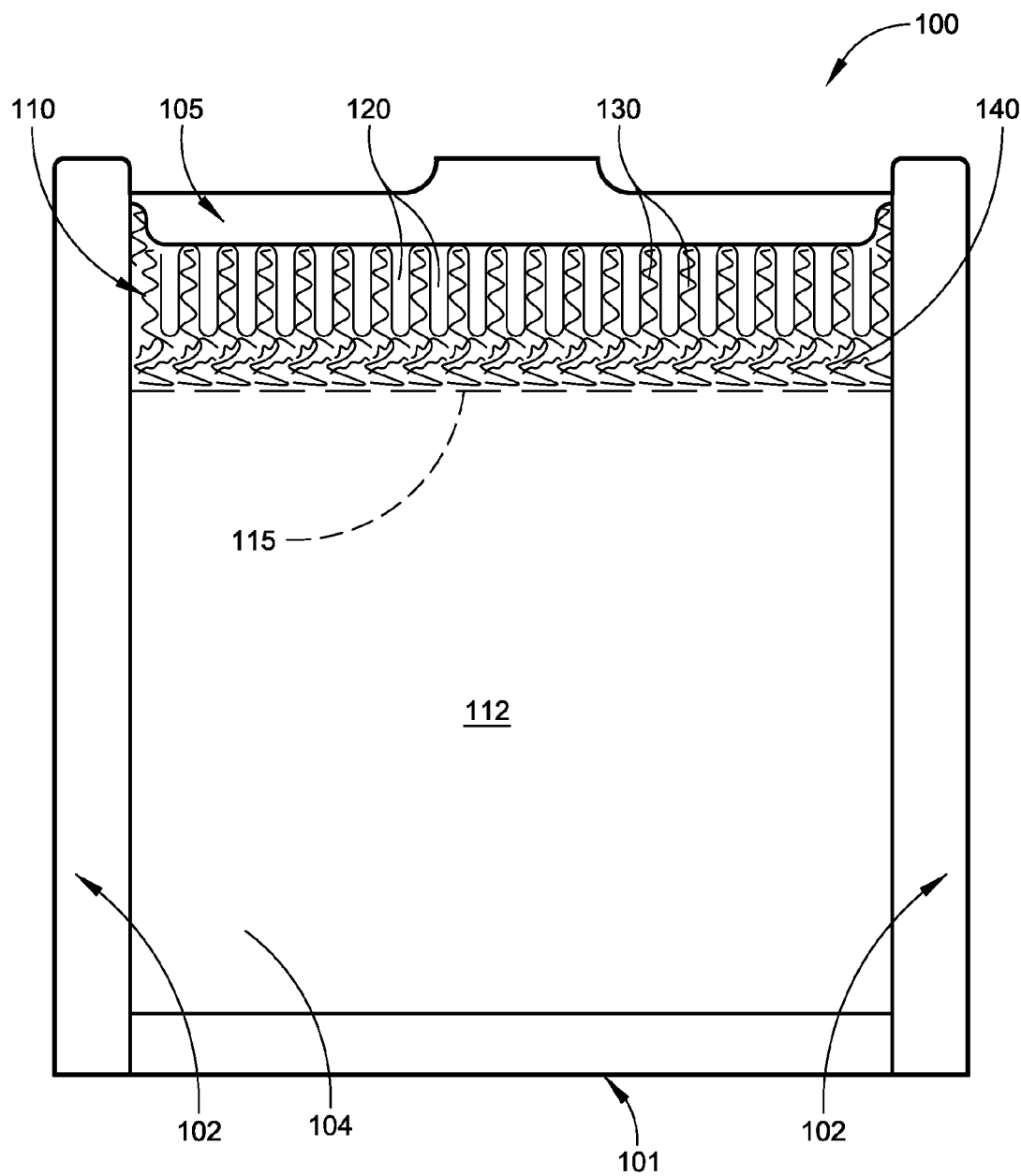
FIG. 1 is a front elevational view of one embodiment of an electrophoresis gel assembly including a visually distinct loading area.

Certain embodiments as disclosed herein provide for an electrophoresis gel having a visually distinct loading area and methods for making such a gel. In one embodiment, for example, the gel material forming the loading area contains an insoluble pigmented material.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

With reference to FIG. 1, an embodiment of an electrophoresis gel assembly 100 having a gel with a visually distinct loading area or portion 110 and a transparent or substantially transparent resolving area or portion 112 is illustrated. Gel assembly is described in more detail below, along with some alternative methods for making the gel. The gel is formed in a mold or cassette 101 having front and rear walls 104, 105 and spacers 102 defining the distance between the walls, as is known in the field. However, unlike known gels, the gel in this embodiment is not completely transparent, but has a loading area or loading portion 110 as indicated in FIG. 1 having transparent or substantially transparent sample wells 120 and a colored area 130, 140 which fills the remainder of the loading portion and completely surrounds the wells. The colored area 130,140 contains a colored gel material, as described in more detail below. The loading area 110 includes seventeen transparent or substantially transparent empty sample wells 120 that are clearly visible in the colored area, making it easy to load samples in the proper place. The loading area 110 has a lower edge 115 which is spaced below the lower ends of the sample wells, so that it is also easy to see the lower ends of the wells both prior to and during loading of samples. Although seventeen sample wells 120 are shown, other numbers of sample wells 120 may be used. Further, the electrophoresis gel assembly 100, the gel itself, and/or the loading area 110 may have other configurations and arrangements than those shown and described herein.

The electrophoresis gel 110, 112 in this embodiment is a generally rectangular slab or layer. The gel material is a composite polymer gel (acrylamide, bis-acrylamide, agarose) in one embodiment, but may be a polyacrylamide gel, an agarose gel containing no acrylamide, or other electrophoresis gel material in other embodiments. The colored gel material in the area 130, 140 may contain an insoluble pigmented or colored material of any suitable color, including white, which does not interfere with electrophoretic separation. In one example, the colored gel material is made using Super Mirror Red TGIC polyester dry powder-coat paint (Columbia Coatings) at 0.2%. The insoluble pigmented material contained in the area 130, 140 which surrounds the sample wells 120 in the loading area 110 is selected to make this area clearly visible. Fine, colored plastic beads are used in one embodiment. The colored plastic beads are polyester dry powder-coat paints in one implementation. Suspensions of such beads in the gel material are useful at various concentrations depending on the color chosen and the desired intensity. In this embodiment, concentrations of colored beads in the range between 0.1 and 1% are used: the lower end of the range is used for intense colors such as bright red, and the upper end of the range for soft colors such as white. The pigment does not move during the separation. Further, polyester dry powder-coat paints do not interfere with the electrophoretic separation.

To make the electrophoresis gel with separate transparent and pigmented or colored portions, the gel is poured in multiple parts, as the plastic beads tend to be denser than the solutions used to make the gel. In the most preferred embodiment, the solution containing the pigment has a density very similar to the pigment itself, which prevents the pigment from settling or floating until the gel is set. Several means can be used to form gels cast in a vertical position, as shown in the following examples.

Example 1

Standard polyacrylamide gels, comprising acrylamide, bis-acrylamide buffers and chemical initiators such as ammonium persulfate and TEMED, are cast in the classical method using a low-density overlay solution, such as 20% ethanol. After the gel has polymerized, the overlay is removed. Another chemically initiated gel-forming solution containing the pigment is added (this solution is often a lower percentage stacking gel, often with a different pH or buffer) and a comb is inserted to form the sample wells 120. Once the second gel has polymerized, the comb is removed. Fingers 130 and lower area 140 below the sample wells 120 are now easy to see. The pigmented area in such methods will not be strongly attached to the remainder of the gel, so it must be tall enough (usually at least 1 cm) so that it does not come out of the mold when the comb is removed.

Example 2

Composite-polymer gels, comprising acrylamide (or N-modified acrylamide), agarose, buffers and photo-initiators with or without a cross-linker such as bis-acrylamide, are cast by filling a mold with one or more gel-forming solutions at elevated temperatures so they are a liquid. Single percentage gels contain only one solution at a constant acrylamide concentration. Gradient gels contain a series of solutions with lower acrylamide concentrations above higher acrylamide concentrations either stepwise or using a mixer to form a continuous gradient from two solutions. In one embodiment, these solutions also include the stacking gel on the top. In any case, the mold is filled to a level just below where the bottom of the well-forming comb will be once inserted. The agarose is allowed to cool and set, but the mold containing the gel-forming solutions is kept from light that would otherwise cause the acrylamide to polymerize. Then, a layer of stacking gel is added containing the pigment, and a comb is inserted. Again, the assembly is allowed to cool so the agarose in this new layer sets. The mold is then exposed to light at the correct wavelength and of sufficient intensity to cause the acrylamide to polymerize. This method forms a gel such that the pigmented loading area 110 does not separate from the remainder or non-pigmented area 112 of the gel.

Example 3

Agarose gels similar to those in Example 2, but not containing acrylamide are formed in the same manner without the final polymerization step. Such gels have a loading area depth greater than the loading area depth in Example 1 to prevent or reduce the risk of the pigmented gel in the loading area from coming out with the comb. The depth of the loading area in this case may be greater than 1 cm.

Example 4

In this method, the gel mold is filled horizontally rather than vertically, using just a single concentration of agarose similar to that in example 3. In this case, the mold is first divided so the well or loading area is blocked and the remainder (e.g. area 112 in FIG. 1) is filled horizontally with the desired gel solution. After this first solution sets, the block is removed and a solution of the same agarose concentration with the pigment is added, and the device to form the holes in the gel surface is added. Once the pigmented solution sets, the well-forming device can be removed and the gel assembly can be used or stored for later use. The same method may be used with other gel-forming solutions, such as composite polymer gels.

Thus, the electrophoresis gel visually differentiates the loading area of the electrophoresis gel, making the sample wells clearly visible and easy to load samples in the proper place.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. An electrophoresis gel, comprising:
   a slab of electrophoresis gel material having opposite edges;
   a sample loading portion extending from one edge of the slab having a plurality of empty sample wells for receiving samples and a gel-containing area surrounding the sample wells;
   a resolving portion extending from the sample loading portion to the opposite edge of the slab and including a gel material; and
   the gel-containing area surrounding the sample wells comprising gel material containing insoluble pigmented material, whereby the entire gel-containing area of the sample loading portion contains insoluble pigmented material and is visually differentiated from the sample wells before samples are loaded into the wells, and the gel material in the resolving portion containing no insoluble pigmented material.

2. The electrophoresis gel of claim 1, wherein the gel material is a composite polymer material.

3. The electrophoresis gel of claim 1, wherein the gel material is selected from the group consisting of: polyacrylamide gel, composite acrylamide and agarose polymer gel, and agarose gel.

4. The electrophoresis gel of claim 1, wherein the insoluble pigmented material comprises colored plastic beads.

5. The electrophoresis gel of claim 4, wherein the colored plastic beads comprise a polyester dry powder-coat paint material.

6. The electrophoresis gel of claim 1, wherein the concentration of insoluble pigmented material in the gel in the sample loading area is between 0.1% and 1%.

7. The electrophoresis gel of claim 1, wherein the wells have inner ends spaced from the resolving portion and the pigmented gel-containing area of the loading portion extends between adjacent wells and between the inner ends of the wells and the resolving portion, the entire gel-containing area of the loading portion comprising gel material which contains insoluble pigmented material and being visually differentiated from the empty sample wells.

8. The assembly of claim 1, wherein the gel material in the resolving area is at least substantially transparent.

9. An electrophoresis gel assembly, comprising:
   a gel holding cassette; and
   a gel in the cassette having a surface, a sample loading portion extending from the surface to a first edge spaced from the surface and a resolving portion extending from the sample loading portion and including a gel material, the loading portion of the gel comprising a plurality of empty sample wells extending from the surface of the gel, and a colored area surrounding the sample wells containing a gel material colored with an insoluble pigmented material and the gel material of the resolving portion containing no insoluble pigmented material;
   whereby the colored area of the sample loading portion is visually differentiated from the empty sample wells prior to loading of samples into the wells.

10. The assembly of claim 9, wherein the colored area extends from the gel surface beyond the ends of the sample wells.

11. The assembly of claim 9, wherein the insoluble pigmented material comprises colored plastic beads.

12. The assembly of claim 11, wherein the colored beads comprise a polyester dry powder-coat paint material.

* * * * *